(12) United States Patent
Duc et al.

(10) Patent No.: US 10,265,151 B2
(45) Date of Patent: Apr. 23, 2019

(54) THREAD INSERTION DEVICES

(71) Applicant: Allergan Industrie SAS, Pringy (FR)

(72) Inventors: Antoine Duc, Saint Jean le Vieux (FR); Bastien Mandaroux, Metz-Tessy (FR)

(73) Assignee: ALLERGAN INDUSTRIE SAS, Pringy (FR)

( * ) Notice: Subject to any disclaimer, the term of this patent is extended or adjusted under 35 U.S.C. 154(b) by 0 days.

(21) Appl. No.: 15/414,306

(22) Filed: Jan. 24, 2017

(65) Prior Publication Data
US 2018/0206967 A1    Jul. 26, 2018

(51) Int. Cl.
*A61F 2/00*    (2006.01)
(52) U.S. Cl.
CPC ................... *A61F 2/0059* (2013.01)
(58) Field of Classification Search
CPC ........................................ A61M 5/00
USPC ............... 623/23.72–23.74; 606/228–231; 604/110, 164.13, 165.01, 198
See application file for complete search history.

(56) References Cited

U.S. PATENT DOCUMENTS

| | | |
|---|---|---|
| 1,250,114 A | 12/1917 | Bigelow et al. |
| 1,558,037 A | 10/1925 | Morton |
| 1,591,021 A | 7/1926 | Davis |
| 2,092,427 A | 9/1937 | Frederick |
| 2,571,653 A | 10/1951 | Victor |
| 3,204,635 A | 9/1965 | Voss |
| 3,674,026 A | 7/1972 | Werner |
| 4,402,308 A | 9/1983 | Scott |
| 4,451,253 A | 5/1984 | Harman |
| 4,820,267 A | 4/1989 | Harman |
| 4,846,886 A | 7/1989 | Fey et al. |
| 4,957,744 A | 9/1990 | della Valle et al. |
| 4,994,028 A | 2/1991 | Leonard |
| 5,211,644 A | 5/1993 | VanBeek et al. |
| 5,215,535 A | 6/1993 | Gettig |
| 5,254,105 A | 10/1993 | Haaga |
| 5,258,013 A | 11/1993 | Granger et al. |
| 5,304,119 A | 4/1994 | Balaban |
| 5,350,385 A | 9/1994 | Christy |

(Continued)

FOREIGN PATENT DOCUMENTS

| | | |
|---|---|---|
| EP | 0648474 A1 | 4/1995 |
| EP | 0809968 A1 | 12/1997 |

(Continued)

OTHER PUBLICATIONS

Bleyer, Mark, SIS Facial Implant 510(k) Summary, Cook Biotech, Inc., May 19, 2005.

*Primary Examiner* — Yashita Sharma
(74) *Attorney, Agent, or Firm* — Nathan S. Smith; Danny Mansour; Morgan, Lewis & Bockius LLP

(57) ABSTRACT

Devices and methods for inserting an implant into skin or other tissue of a patient can include an insertion device having moveable portions that can retain, move, or otherwise control engagement and injection of a hyaluronic thread. The device can include a tubular member and a handle. The handle can include two or more components that each include apertures through which a needle can be placed. The handle can be manipulated to align or offset the apertures with respect to each other to modify a clearance through the apertures and selectively engage or disengage the needle or thread.

27 Claims, 7 Drawing Sheets

(56) References Cited

U.S. PATENT DOCUMENTS

| | | |
|---|---|---|
| 5,366,447 A | 11/1994 | Gurley |
| 5,478,327 A | 12/1995 | McGregor et al. |
| 5,599,293 A | 2/1997 | Orenga |
| 5,735,827 A | 4/1998 | Adwers |
| 5,824,335 A | 10/1998 | Dorigatti et al. |
| 5,997,513 A | 12/1999 | Smith |
| 6,102,920 A | 8/2000 | Sullivan |
| 6,159,233 A | 12/2000 | Matsuzawa |
| 6,162,203 A | 12/2000 | Haaga |
| 6,214,030 B1 | 4/2001 | Matsutani et al. |
| 6,450,937 B1 | 9/2002 | Mercereau |
| 6,547,762 B1 | 4/2003 | Botich |
| 6,936,297 B2 | 8/2005 | Roby et al. |
| 7,041,088 B2 | 5/2006 | Nawrocki et al. |
| 7,504,386 B2 | 3/2009 | Pressato et al. |
| 7,559,952 B2 | 7/2009 | Pinchuk |
| 7,666,339 B2 | 2/2010 | Chaouk et al. |
| 7,722,582 B2 | 5/2010 | Lina et al. |
| 8,177,792 B2 | 5/2012 | Lubock |
| 8,652,216 B2 | 2/2014 | Chen |
| 9,801,688 B2 | 10/2017 | Jones |
| 2001/0008937 A1 | 7/2001 | Callegaro et al. |
| 2001/0050084 A1 | 12/2001 | Knudson |
| 2002/0026039 A1 | 2/2002 | Bellini et al. |
| 2003/0023250 A1* | 1/2003 | Watschke .......... A61B 17/0469 606/148 |
| 2003/0097079 A1 | 5/2003 | Garcia |
| 2003/0109769 A1 | 6/2003 | Lowery |
| 2004/0192643 A1 | 9/2004 | Pressato et al. |
| 2005/0033362 A1 | 2/2005 | Grafton |
| 2005/0075606 A1 | 4/2005 | Botich |
| 2005/0182446 A1 | 8/2005 | DeSantis |
| 2006/0041320 A1 | 2/2006 | Matsuda |
| 2006/0136070 A1 | 6/2006 | Pinchuk |
| 2008/0125766 A1 | 5/2008 | Lubock |
| 2008/0139928 A1 | 6/2008 | Lubock |
| 2008/0167674 A1 | 7/2008 | Bodduluri et al. |
| 2009/0131908 A1 | 5/2009 | McKay |
| 2009/0209804 A1 | 8/2009 | Seller |
| 2009/0318875 A1 | 12/2009 | Friedman |
| 2010/0256596 A1 | 10/2010 | Chomas |
| 2011/0093088 A1 | 4/2011 | Chen |
| 2011/0263724 A1 | 10/2011 | Gurtner et al. |
| 2011/0282447 A1 | 11/2011 | Niu |
| 2012/0108895 A1 | 5/2012 | Neuman |
| 2012/0215230 A1 | 8/2012 | Lubock et al. |
| 2013/0122068 A1 | 5/2013 | Fermanian et al. |
| 2013/0211374 A1 | 8/2013 | Hetherington |
| 2013/0226235 A1 | 8/2013 | Fermanian et al. |
| 2013/0274222 A1 | 10/2013 | Horne et al. |
| 2013/0310750 A1 | 11/2013 | Hopman |
| 2014/0221940 A1 | 8/2014 | Clauson et al. |
| 2014/0228971 A1 | 8/2014 | Kim |
| 2015/0209265 A1 | 7/2015 | Horne |
| 2015/0209523 A1 | 7/2015 | Horne et al. |
| 2015/0327972 A1 | 11/2015 | Horne et al. |
| 2016/0007990 A1 | 1/2016 | Solish et al. |
| 2016/0074307 A1 | 3/2016 | Gurtner et al. |
| 2016/0213813 A1 | 7/2016 | Gurtner et al. |
| 2017/0049972 A1 | 2/2017 | Persons |
| 2017/0156754 A1 | 6/2017 | Valbuena |
| 2017/0290987 A1 | 10/2017 | Mandaroux et al. |
| 2018/0206963 A1 | 7/2018 | Duc et al. |
| 2018/0206964 A1 | 7/2018 | Duc et al. |
| 2018/0206965 A1 | 7/2018 | Duc et al. |
| 2018/0206966 A1 | 7/2018 | Due et al. |

FOREIGN PATENT DOCUMENTS

| | | |
|---|---|---|
| EP | 2422832 A2 | 2/2012 |
| EP | 2103262 B1 | 2/2013 |
| EP | 2184016 A4 | 4/2013 |
| EP | 2671516 A1 | 12/2013 |
| GB | 2336783 A | 5/2003 |
| KR | 20120007473 A | 1/2012 |
| KR | 101246570 B1 | 3/2013 |
| KR | 20130036921 A | 4/2013 |
| KR | 20130130436 A | 12/2013 |
| KR | 20130132196 A | 12/2013 |
| KR | 20140029007 A | 3/2014 |
| WO | 199001349 A1 | 2/1990 |
| WO | 1992013579 A1 | 8/1992 |
| WO | 200100190 A2 | 1/2001 |
| WO | 2004022603 A1 | 3/2004 |
| WO | 2006065837 A2 | 6/2006 |
| WO | 2010028025 A1 | 3/2010 |
| WO | 2011109129 A1 | 9/2011 |
| WO | 2011109130 A1 | 9/2011 |
| WO | 2012054301 A1 | 4/2012 |
| WO | 2012054311 A1 | 4/2012 |
| WO | 2013055832 A1 | 4/2013 |
| WO | 2013082112 A1 | 6/2013 |
| WO | 2012174464 A3 | 5/2014 |
| WO | 2015105269 A1 | 7/2015 |

* cited by examiner

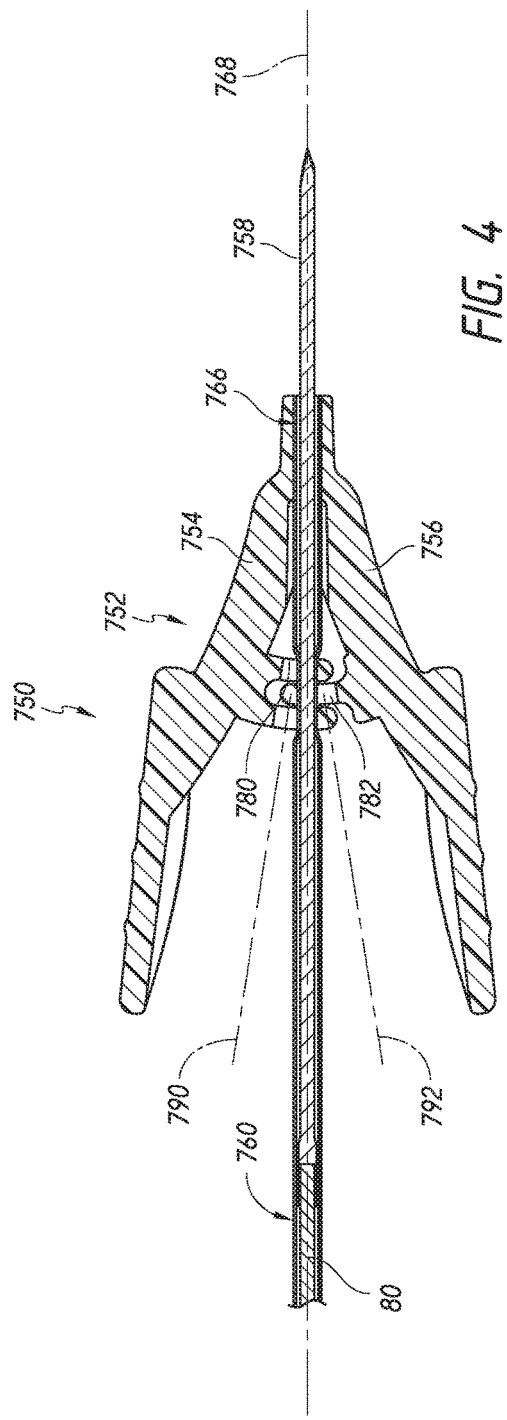
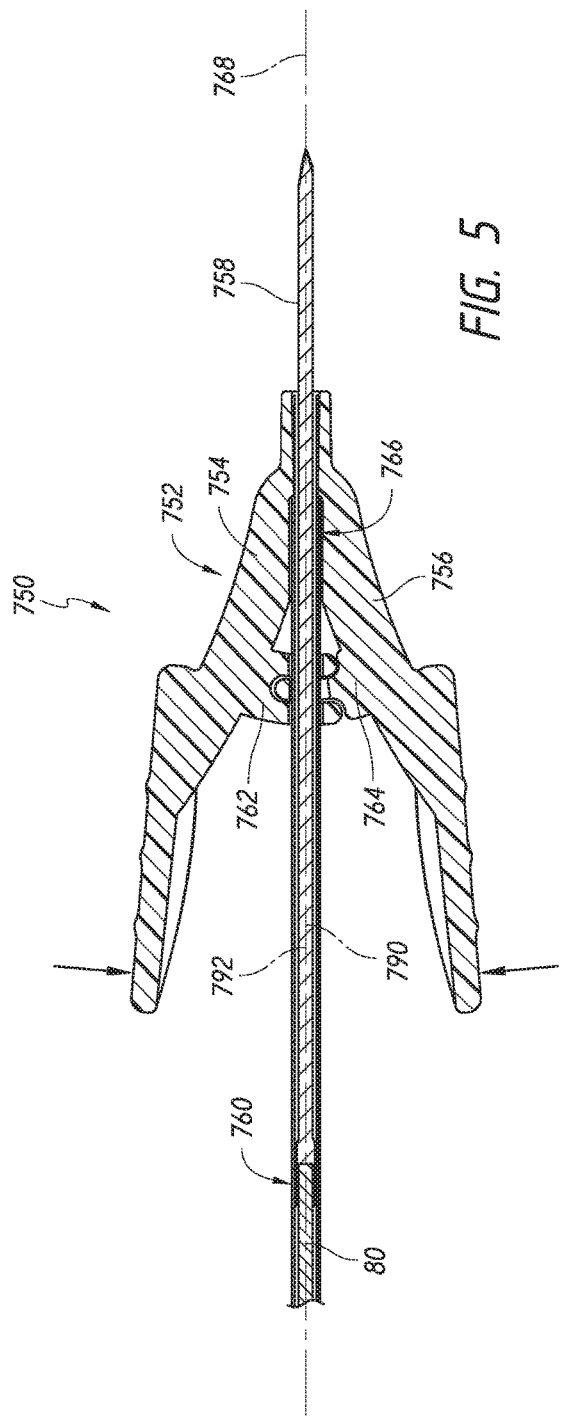

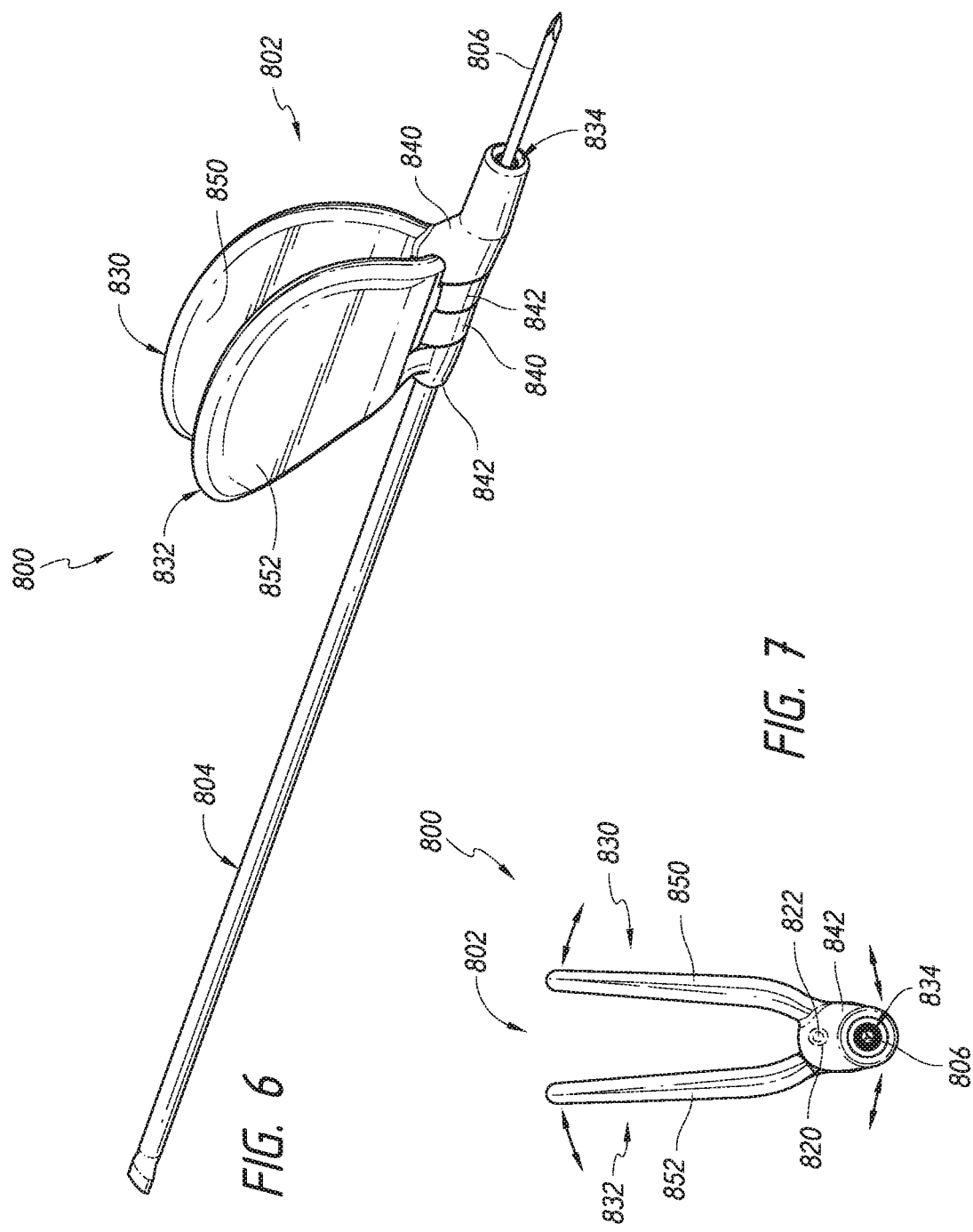

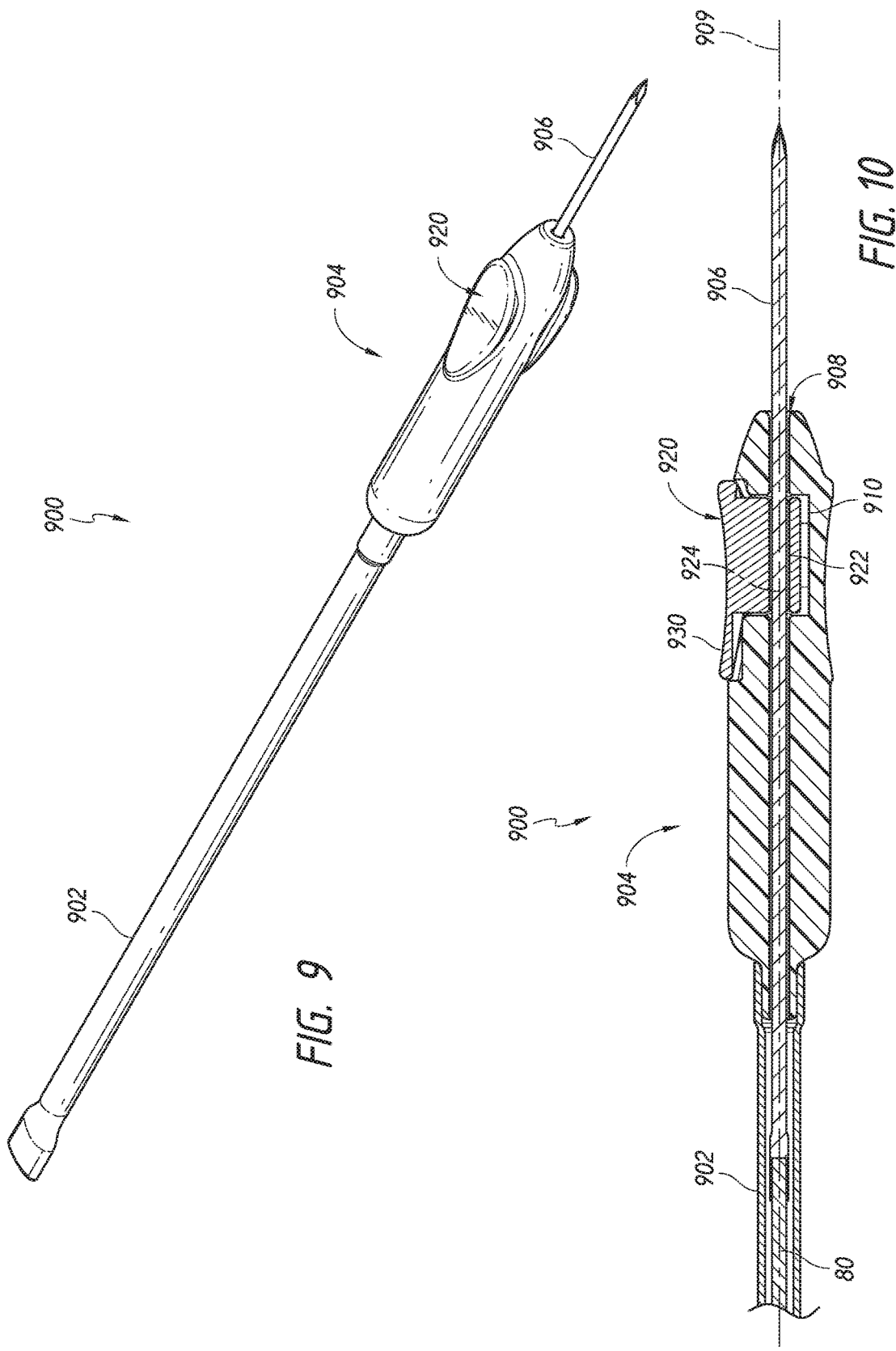

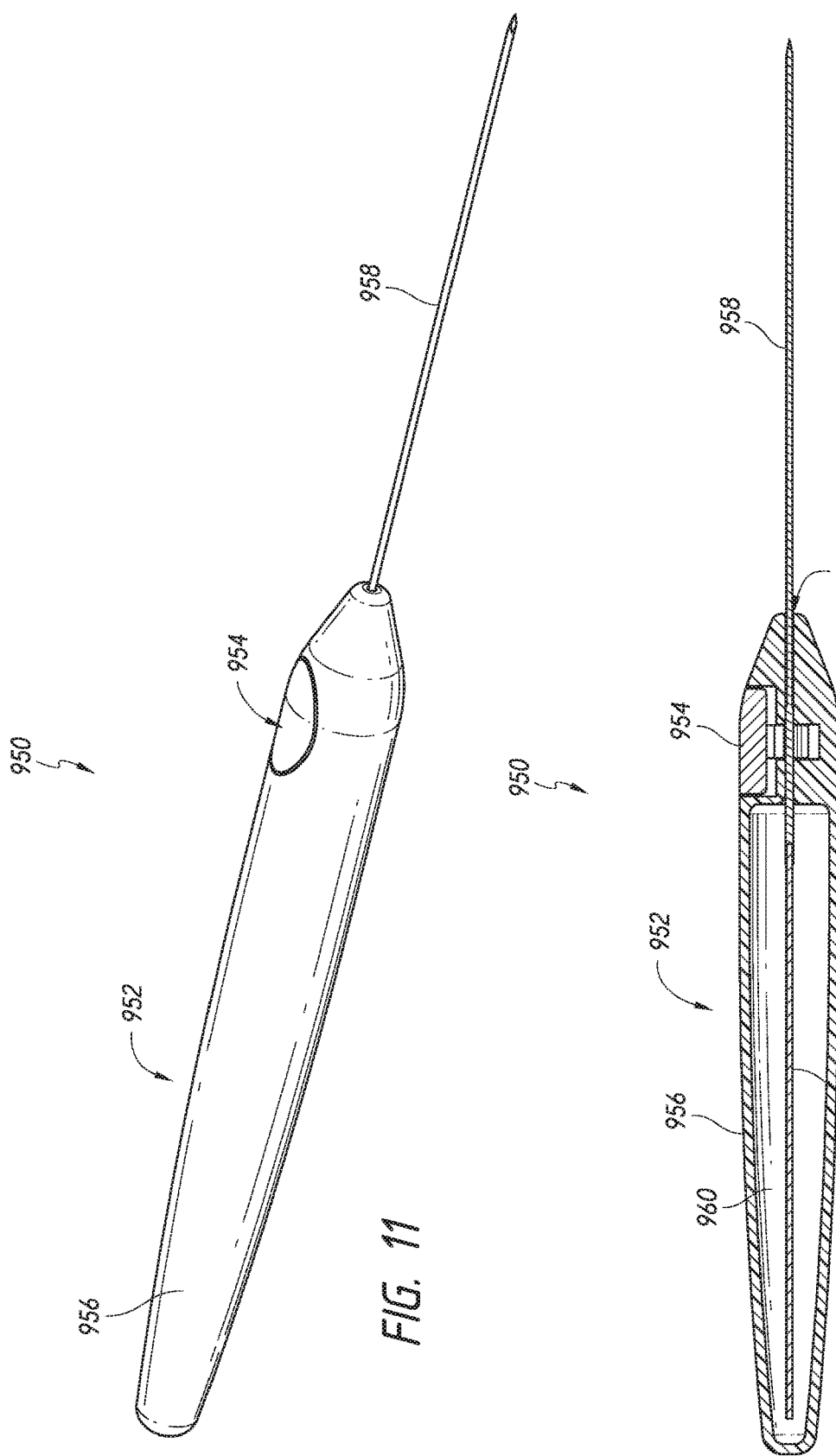

THREAD INSERTION DEVICES

BACKGROUND

Field of the Inventions

The present disclosure relates generally to systems and methods for insertion of an implant, and more particularly, to insertion devices that can protect and grasp a needle or thread to enable to physician to insert of the thread into skin or other tissue.

Background

In recent years, millions of men and women have elected to receive dermal filler injections to rejuvenate aging skin and look younger without surgery or significant downtime. A dermal filler injection is a procedure through which a gel-like, volumizing substance is injected subcutaneously to restore lost volume, add volume to facial features and contours, or smooth fine lines and creases.

Some dermal filler injections are performed using a thread or other implant. Once inserted, the threads used for dermal filler injections can hydrate and expand or swell within the skin of a patient, thereby lessening the appearance of wrinkles, folds, and/or sagging portions of skin.

To insert a thread into the patient, conventional suture procedures can be implemented. For example, using a conventional procedure, a physician couples a thread to a needle and inserts the needle through the skin until achieving a desired placement, which may be adjacent to or under a wrinkle. With the thread placed along or underneath the wrinkle, the needle can be removed and as the thread hydrates, the wrinkle can be "filled" and become less prominent, thus smoothing the skin and achieving a desired aesthetic for the patient.

SUMMARY

The present application discloses various improvements for thread insertion devices and related procedures that can be used to treat humans and/or animals. The devices and procedures can be used, for example, in the context of dermal fillers, surgery (e.g., placing sutures), drug delivery, negative pressure wound therapy, and wound dressing.

In plastic surgery, hyaluronic acid is a common substance used for wrinkle filling. Although hyaluronic acid is typically used as a gel that is injected as a wrinkle filler, some embodiments disclosed herein can utilize hyaluronic acid in a solid form as an implant, e.g., as a hyaluronic acid thread ("HA thread" or "thread").

However, in accordance with some embodiments disclosed herein in the realization that because HA threads are hydrophilic, the mechanical integrity of the thread can rapidly degrade during an implantation procedure. Thread failure can result in improper placement or other complications during the procedure. Thus, a thread that is exposed during insertion of the thread into a patient can become hydrated, causing the thread to swell or expand prematurely and/or lose its tensile strength. If the thread swells within a needle or insertion device, the thread will become lodged within the needle and unable to move relative to the insertion device. The thread can therefore block the needle lumen, prevent separation of the thread from the insertion device, or otherwise complicate the thread placement procedure. In some instances, the swelling of a thread may cause it to engage with skin tissue before the thread has reached a desired position subcutaneously. Thus, the thread becomes immovable during insertion of the thread into the patient. Further, during insertion, friction between the thread and the tissue may increase beyond a tensile strength of the thread and cause the thread to break and separate from the insertion device.

Further, some embodiments of the present devices and methods also contrast with various conventional thread placement devices that include a needle tip that engages a thread at its midsection and allows the thread to fold backwardly or proximally along a length of the needle. In accordance with some embodiments disclosed herein in the realization that because the thread is divided into two strands that extend along the length of the needle, the injection also results in a double-stranded thread placement in which the two strands will swell in situ. Although this may be acceptable in some applications, these conventional devices and procedures are limited because they have a "minimum expansion size" of twice that of a single thread. Accordingly, some of the embodiments disclosed herein enable a single strand of thread to be placed along a desired position instead of the conventional double-stranded thread placement. Advantageously then, some embodiments allow for a lower "minimum expansion size" that can allow a physician to treat wrinkles that are not otherwise good candidates for treatment using only the conventional devices or methods.

Further, because some embodiments disclosed herein "push" a distal end of the thread through the skin, the physician need only to make a single piercing instead of entry and exit piercings required by conventional devices and methods that use a needle whose proximal end attaches to a distal end of the thread and pulls the thread through the entry and exit piercings.

Therefore, some embodiments of the thread insertion devices and procedures disclosed herein can advantageously minimize the number of piercings through the skin, reduce the risk of thread contamination during the insertion procedure, and/or minimize pain and bruising to the patient. Further, some embodiments of the thread insertion devices and procedures disclosed herein can advantageously avoid breakage of the thread during insertion, facilitate safer and easier insertion of the thread, and/or permit greater control over the thread length and insertion depth.

Although particular embodiments of the present disclosure may be disclosed in the context of an implant comprising a thread, it is contemplated that embodiments can be used with various implants. For example, embodiments can be used with an implant comprising a thread, a series of hinged members, or a tube. Further, embodiments can comprise an implant comprising a rigid material, a flexible material, HA threads material, and a material comprising a state of matter including solid, liquid, or any state there between. The implant can comprise a medication and/or medical fluid that are configured to be released by the implant.

In some embodiments, the thread insertion device can comprise a cover member configured to protect an implant, or portions of a device that will be inserted into a patient. The cover member can prevent contamination or damage to a thread. The cover member can also maintain a shape or alignment of a thread relative to a thread insertion device.

The cover member can comprise a cavity or passage configured for a thread to be positioned therein. For example, the cover member can retain at least a portion or an entirety of the thread within a cavity or passage. Contamination or damage to the thread can be prevented when the thread is positioned within a cavity or passage of the cover member. The cover member can prevent contamination of the thread from exposure to an ambient environment, or from a person touching the thread. Further, damage to the thread can be avoided by preventing inadvertent touching or engagement of the thread. Damage to the thread can also be avoided by preventing exposure of the thread to moisture from the patient's skin or tissue, e.g., dermis, epidermis, and subcutaneous tissue, during insertion of the thread.

In some embodiments, the cover member can permit a thread to be positioned along an outer surface of the cover member. The cover member can permit a thread to be positioned along an inner surface of the cover member. The cover member can also provide support to maintain alignment of the thread during insertion.

In some embodiments, the thread can be retained and/or engaged with the cover member and/or a portion of the thread insertion device. Further, the cover member and/or a portion of the thread insertion device can be used to move a thread relative to the insertion device or separate a thread from the insertion device.

For example, the insertion device can comprise one or more portions that extend along an outer surface and/or within the cover member. The thread insertion device can comprise a moveable member within the cover member. A piston can be positioned within a cavity of the cover member. The piston can cause movement of the thread supported on or coupled with the insertion device. Movement of a portion of the insertion device, e.g., the cover member and/or the piston, can release or separate a thread from the insertion device.

In some embodiments, the thread insertion device can comprise a cover member that can be engaged against a thread to retain the thread with the insertion device. A portion of the cover member can be crimped, or compressed, or adhered to engage a portion of a thread. The thread can be adhered to the cover member. To release a thread from the insertion device, a portion of the cover member engaged against a thread can be moved or expanded, or the thread can be separated from the portion of the cover member.

The cover member can comprise a flexible or rigid body. The body can comprise a cross-sectional profile that defines a cavity. A shape of a cross-sectional profile of the cover member can comprise an open perimeter, a closed perimeter, a circle, a square, a rectangle, an L-shape, and/or a U-shape. The cover member can comprise an inner surface cross-sectional profile having portions that are tubular along a length of the cover member.

A portion of the cover member can comprise an opening, e.g., a channel or an aperture, between an inner cavity and an outer surface of the cover member. The cover member can permit a thread to be moved through the opening. A thread can be coupled to the insertion device by a portion of the thread that extends through the opening.

The cover member can comprise a proximal portion and a distal portion. The proximal portion can comprise an opening into a cavity of the cover member. The proximal portion can be coupled to other portions of the thread insertion device. The proximal portion can be releasably coupled to a portion of the insertion device.

A cavity of the cover member can extend toward the distal portion of the cover member. The cavity can extend toward a closed distal portion of the cover member. The distal portion of the cover member can comprise a tip portion. The tip portion can comprise an outer surface that tapers toward a point. A tapered or pointed tip can permit the cover member to pierce the patient's skin or tissue to allow insertion of the cover member and thread. The tip can comprise a point, a bevel, or a multiple-sided cutting point, e.g., a pin, a needle, or a trocar. The tip portion can comprises an outer surface that is rounded or blunt. A round or blunt tip can permit insertion of the cover member through an opening of a patient without piercing or causing damage to the patient.

The thread insertion device can comprise a handle to engage or release a portion of the insertion device. The handle can be moved, relative to the insertion device, to engage or release a portion of the insertion device. A portion of the handle can be configured to be held by a physician and moved relative to the insertion device.

A needle can be positioned within the insertion device between portions of the handle. Movement of the handle can cause a portion of the insertion device to engage the needle. The needle can comprise a proximal portion and a distal portion, opposite the proximal portion. The needle can be positioned with the proximal portion between portions of the handle, and the distal portion extending from the insertion device. A thread can be coupled to the proximal portion of the needle.

The handle can comprise a moveable portion configured to be urged or move relative the handle or the insertion device. The moveable portion can comprise an arm, a lever, a button, and/or a moveable member. The moveable portion can be urged toward or away from the insertion device. Urging the moveable portion toward the insertion device can cause a portion of the handle to extend into a lumen of the insertion device. Urging the moveable member toward the insertion device can cause a portion of the handle to move away from a lumen of the insertion device.

The handle can comprise a moveable member configured to intersect a lumen that extends through the handle. The moveable member can be positioned to engage a needle positioned within the lumen, thereby preventing movement of the needle along an axial length of the lumen. The moveable member can be moved to disengage from the needle and permit movement of the needle along an axial length of the lumen.

The handle can comprise an arm to permit and/or prevent movement of a needle relative to the insertion device. The arm can extend from the insertion device, and can be moved by urging the arm toward or away from the insertion device. A portion of the arm or handle can engage a needle positioned within the insertion device when the arm is urged, thereby preventing movement of the needle relative to the insertion device. Optionally, a portion of the arm or handle can release a needle positioned within the insertion device when the arm is urged, thereby permitting movement of the needle relative to the insertion device.

The handle can comprise first and second arms that extend from the insertion device. A portion of the first and second arms can engage a needle positioned within the insertion device when the first and second arms are urged toward each other. Each arm of the handle can comprise a first portion that extends away from the insertion device, and a second portion, e.g., a gripping mechanism, that extends from the first portion toward the insertion device. The gripping mechanism of each arm can overlap each other and intersects a lumen of the insertion device. In a first configuration, the first and second arms can be biased away from each other to engage a needle within the lumen. In a second configuration, the first and second arms can be urged further toward each other to release the needle within the lumen.

The thread insertion device can comprise a tubular member to prevent contamination or damage to a thread and/or needle. The tubular member can maintain a shape or alignment of a thread relative to a thread insertion device. The tubular member can comprise an envelope, a sleeve, and/or a cavity configured to retain a thread therein. The tubular member can comprise a rigid material, flexible material, and/or a heat-shrinkable material.

The tubular member can be a tube configured to restrict movement of a thread, positioned within the tubular member, along a longitudinal axis of the thread. The tubular member can comprise an inner cross-sectional profile approximately equal to a cross-sectional profile of a thread to permit movement of the thread within the tubular member. The tubular member can comprise a cavity to permit a thread to be gathered within the cavity. As the thread, or needle coupled to the thread, can be directed away from the insertion device, the portion of the thread gathered within the cavity can be withdrawn from the tubular member.

The tubular member can be formed as a portion of the insertion device or coupled to the insertion device. Optionally, a portion of the tubular member can comprise a portion of a handle. The tubular member can comprise a proximal portion and a distal portion, opposite the proximal portion. The distal portion can be coupled to the insertion device to form a cavity that extends from the insertion device toward the tubular member. The distal portion can be coupled to a handle or a base of the insertion device. Optionally, the tubular member can comprise a cover member.

The thread insertion device can comprise a cap to enclose a portion of a thread or a needle. The cap can be removably coupled with a handle to enclose a portion of a needle extending from a handle, thereby preventing inadvertent contact or contamination of the needle.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures:

FIGS. 4 and 5 are cross-sectional side detail views of an insertion device, according to some embodiments.

FIG. 6 is a front perspective view of an insertion device, according to some embodiments.

FIG. 7 is a front view of an insertion device, according to some embodiments.

FIG. 9 is a front perspective view of an insertion device, according to some embodiments.

FIG. 10 is a cross-sectional side detail view of an insertion device, according to some embodiments.

FIG. 11 is a front perspective view of an insertion device, according to some embodiments.

FIG. 12 is a cross-sectional side view of an insertion device, according to some embodiments.

DETAILED DESCRIPTION

Figure 1:
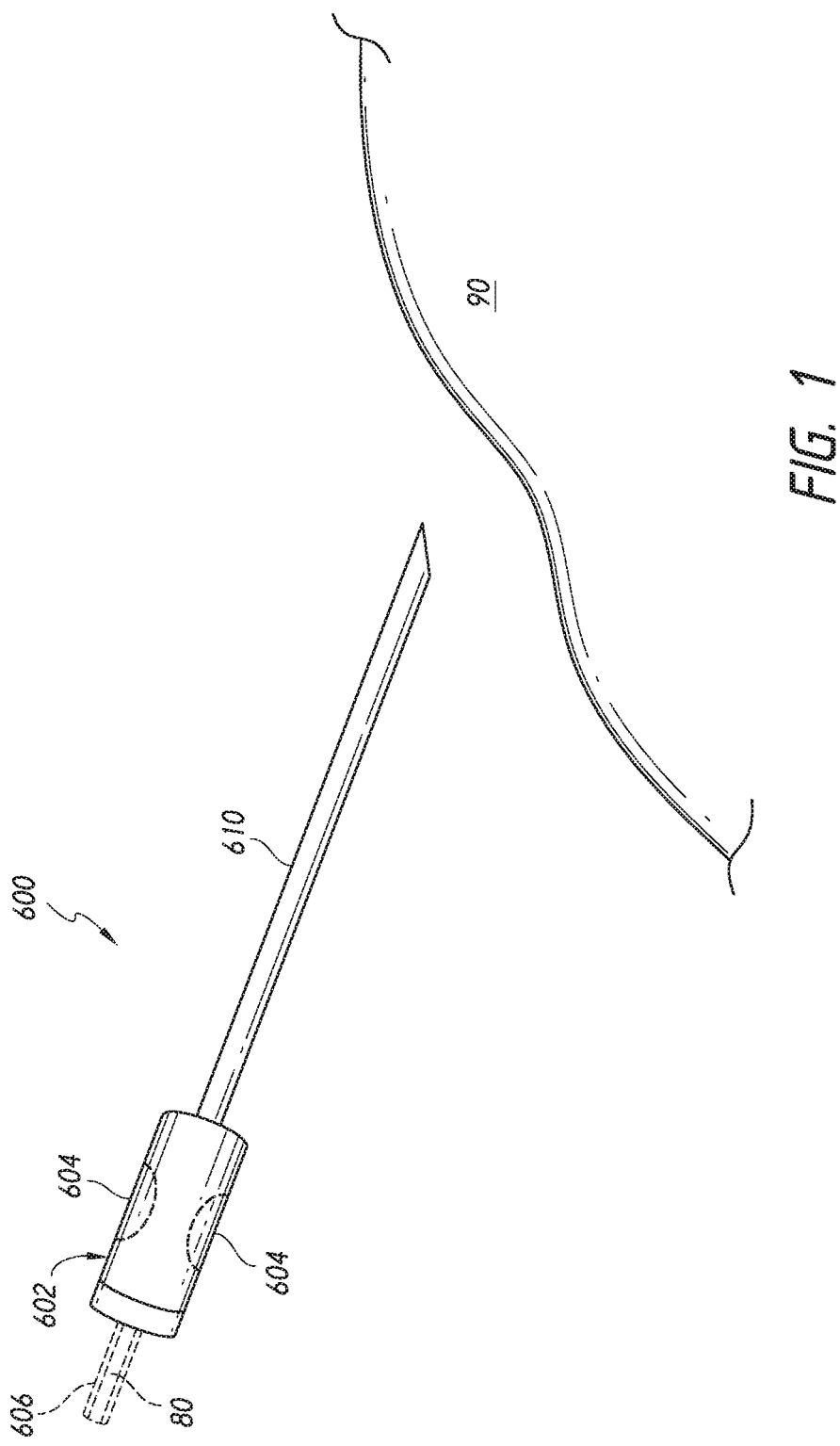
FIG. 1 is a front view of an insertion device, according to some embodiments.
Figure 2:
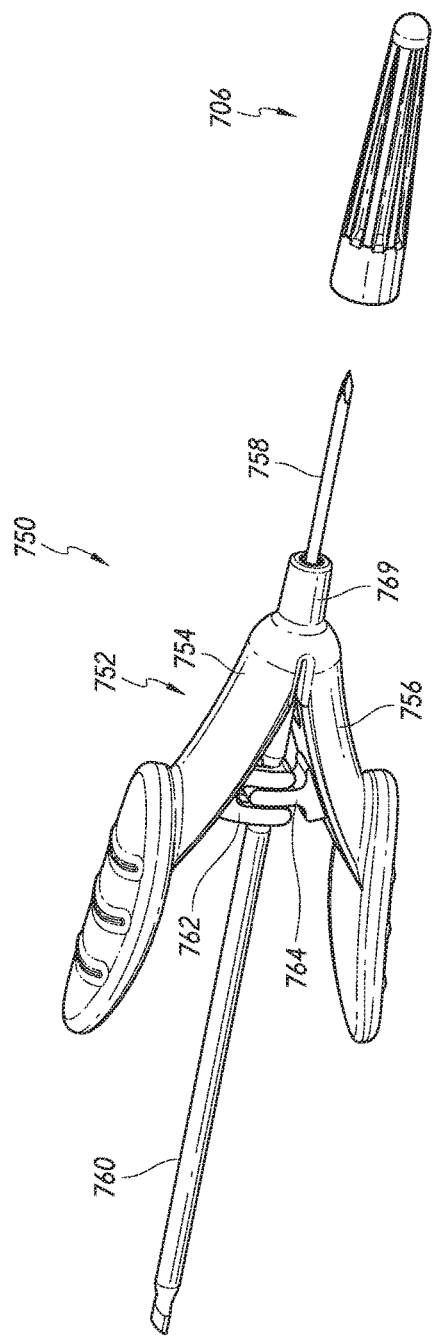
FIG. 2 is a front perspective view of an insertion device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of HA thread insertion devices, such embodiments can be used with various devices and implants. Furthermore, various applications of such embodiments and modifications thereto, which may occur to those who are skilled in the art, are also encompassed by the general concepts described herein.

The present application addresses several operational challenges encountered in prior HA thread insertion devices and related procedures. This application provides numerous improvements that enable the physician to control the device more easily, thereby allowing precise positioning of the implant while minimizing trauma to the patient.

For example, in accordance with some embodiments, the present application discloses various features and advantages of thread insertion devices and procedures that can be used to deliver an implant into skin or other tissue of a patient. The thread insertion device can avoid contamination a HA thread and protect the thread's mechanical properties during insertion. The thread insertion device can also permit a physician to precisely position the implant while minimizing trauma to the patient. The present disclosure, along with co-pending U.S. patent application Ser. Nos. 15/414,195, 15/414,248, 15/414,278, and 15/414,219, each filed on the same day as the present application, includes various features that can be interchangeably implemented into embodiments of thread insertion devices and methods of their use and the contents of these applications are incorporated herein in by reference in their entireties. For example, various aspects of the engagement mechanisms, actuation components, cover members, handles, and other features for delivering, protecting, engaging, advancing, or otherwise handling a needle and/or thread, can be combined or substituted with features of embodiments disclosed herein.

Further, some embodiments of the thread insertion devices and procedures disclosed herein can advantageously allow a single strand of HA thread to be positioned in situ as opposed to conventional double-stranded thread placement. In some embodiments, needle insertion devices can be provided that can engage a needle and/or thread in order to permit a physician to advance the needle and/or thread into a patient.

As discussed above, a HA thread can be used as a dermal filler to treat wrinkles. This solution is of particular interest to treat long and thin wrinkles in very localized and continuous manner. HA threads could be used on various points of correction on the neck, face, decolletage, hands, or other such areas.

In some embodiments, thread insertion procedures can be performed using a needle or trocar directly attached to a HA thread in a suture-like arrangement. The HA thread can be placed linearly under the wrinkle and pulled through the skin in a suture-like process using the needle. The injection requires the needle to pierce the skin at an entry point, to be advanced subcutaneously until the thread is pulled and positioned subcutaneously, and then to pierce the skin a second time at an exit point to withdraw the needle. The thread and the needle can be separated by twisting the wired thread until it breaks.

The present disclosure provides a variety of needle insertion devices that provide greater control, ease of use, reduced risk of contamination, and better protection of the thread than prior devices and procedures. For example, some of the needle insertion devices disclosed herein can enable a physician to securely grasp the needle using a device, separated from the thread, that is releasably attachable to the needle. Some embodiments of the devices can move between a first configuration in which components of the device are positioned along a passage wherethrough the needle or trocar passes to define a first cross-sectional clearance, and a second configuration in which a portion of at least one of the components extends into, compresses, or otherwise obstructs the passage to define a second cross-sectional clearance, different from the first cross-sectional clearance, to thereby change a cross-sectional profile of the passage. The first cross-sectional clearance can be less than or greater than the second cross-sectional clearance, which can allow needle to be selectively engaged by the components of the device.

For example, referring now to FIG. 1, a schematic illustration of an embodiment of a needle or thread insertion device 600 is illustrated. The insertion device 600 can comprise a handle 602, a moveable portion 604, and a tubular member 606. The tubular member 606 can be coupled to a proximal end of the handle 602. The needle 610 can be coupled at its proximal end to a HA thread 80 that extends within the tubular member 606. Further, a trocar or needle 610 can extend through a passage of the handle 602 to be releasably engaged by the moveable portion 604 to permit or restrict movement of the needle 610 relative to the handle 602 and the tubular member 606.

In accordance with some embodiments, the handle 602 can be configured to engage with the needle 610 and/or the thread 80 to permit the physician to advance the needle 610 into the patient and thereafter release the needle 610 and/or the thread 80.

The handle 602 can comprise a passage that extends through proximal and/or distal portions of the handle 602. The tubular member 606, the needle 610, and/or the thread 80 can extend through the passage of the handle 602. As discussed further herein, the size of the passage can be changed, e.g., increased or reduced, to selectively engage or release the tubular member 606, the needle 610, and/or the thread 80 extending through the passage to permit movement of the needle 610 and/or the thread 80 through the passage, relative to the insertion device 600.

The needle 610 can have a proximal portion and a distal portion. The distal portion of the needle 610 can comprise an outer surface that tapers toward a pointed tip to pierce the tissue and/or skin 90 of a patient. The distal portion of the trocar 610 can also comprise a rounded or blunt surface. Further, as noted above, the needle 610 can comprise a trocar having a three-sided cutting point or tip.

A portion of the thread 80, e.g., a distal portion, can be attached or coupled to the proximal portion of the needle 610. For example, the proximal portion of the needle 610 can comprise a cavity or pocket. The cavity can receive and be coupled to a distal portion of the thread 80. The thread 80 can be coupled to the needle 610 mechanically or by using an adhesive such as, for example, glue, tape, or other solutions to engage the proximal portion of the needle 610 with the thread 80.

The tubular member 606 can enclose, house, or be coupled to a portion of a needle and/or the thread 80. For example, the tubular member 606 can comprise a tube, an envelope, and/or a sleeve that defines an inner surface and lumen that extends between proximal and/or distal portions of the tubular member 606. The lumen can be configured to permit the needle 610 and/or thread 80 to be positioned therein. In some embodiments, the cavity of the tubular member 606 can be used to protect the thread 80 from contamination prior to and during the injection procedure. Additionally, the tubular member 606 can permit the thread to be stored or gathered within a cavity of the tubular member 606. Further, the tubular member 606 can comprise a rigid material, flexible material, and/or a heat-shrinkable material.

The lumen of the tubular member 606 can have a cross-sectional profile, transverse to the longitudinal axis of the tubular member 606, which can comprise a circle, oval, regular or irregular polygon, square, and/or rectangle shape. The cross-sectional profile of the tubular member 606 can have a size that is at least approximately equal to an outer cross-sectional profile of the needle 610 and/or thread 80 to permit movement of the thread 80 and/or needle within the tubular member 606 (when not crimped or constricted).

The insertion device 600 can be actuated to engage or disengage with the needle 610 and/or the thread 80 using the handle 602. The handle 602 can be disposed at a distal portion of the tubular member 606. In some embodiments, the handle 602 can be formed with the tubular member 606 as a single component or unitarily as a single, continuous piece of material. However, as illustrated, the handle 602 can be formed as a separate component that is coupled to the tubular member 606. The handle 602 can be configured to extend along the lumen or a portion of the outer surface of the tubular member 606.

In some embodiments, the handle 602 can comprise at least one moveable portion 604. The movable portion 604 can comprise an arm, lever, button, and/or movable member that can be deflected or moved by the physician relative to the passage of the handle 602 to decrease or increase the size of the passage. The change in size of the passage of the handle 602 thereby directly or indirectly engages or disengages the device 600 with the tubular member 606, the needle 610, and/or the thread 80. In some embodiments, the moveable portion 604 can comprise first and second moveable portions that are moveable relative to each other.

For example, in some embodiments, compressing the moveable portion(s) 604 toward a longitudinal axis of the insertion device 600 can cause a portion of the movable portion 604 and/or the handle 602 to be urged toward and/or into the passage to engage with the needle 610, the tubular member 606, and/or the thread 80.

However, in other embodiments, compressing the moveable portion(s) 604 toward a longitudinal axis of the insertion device 600 can cause a portion of the movable portion 604 and/or the handle 602 to extend out of the passage to permit the needle 610, the tubular member 606, and/or the thread 80 to move freely within the passage and/or to become disengaged from the handle 602.

Further, in some embodiments in which the tubular member 606 extends at least partially through the passage of the handle 602, the movable portion 604 can engage with or release the tubular member 606 to crimp down onto or release the needle 610 and/or thread 80 disposed within the lumen of the tubular member 606. For example, the tubular member 606 can be deflected, crimped, and/or resiliently move between a clear-through lumen state and constricted lumen state to permit or restrict movement of a thread or needle positioned therein along a longitudinal axis of the thread.

Accordingly, the physician can selectively actuate the movable portion 604 of the handle 602 in order to engage or disengage the needle 610 and/or thread 80 during the injection procedure.

Referring now to FIGS. 2-5, an embodiment of a needle insertion device is illustrated that can engage with a needle in a default state to allow a physician to advance the needle and the thread to a desired position in situ without requiring the physician to exert a pinching or compression force. The insertion device can then be pinched or compressed to release or disengage with the needle. FIGS. 2-5 illustrate a needle insertion device 750 that can comprise a handle 752 having a first arm 754 and a second arm 756 extending from the handle 752 that can be used to engage a needle 758 coupled to a HA thread 80. The insertion device 750 can also comprise a tubular member 760 that can be coupled to the handle 752 or formed therewith to protect the thread 80.

For example, the tubular member 760 can enclose, house, or be coupled to a portion of a needle and/or a HA thread 80. The tubular member 760 can be coupled to the handle 752 or be formed therewith. For example, the tubular member 760 can comprise a tube, an envelope, and/or a sleeve that defines an inner surface and lumen that extends between proximal and/or distal portions of the tubular member 760. The lumen can be configured to permit the needle 758 and/or thread 80 to be positioned therein. In some embodiments, the cavity of the tubular member 760 can be used to protect the thread 80 from contamination prior to and during the injection procedure. A proximal portion of the tubular member 760 can be crimped, compressed, or glued to close the proximal portion of the lumen.

The lumen of the tubular member 760 can have a cross-sectional profile, transverse to the longitudinal axis of the tubular member 760, which can comprise a circle, oval, regular or irregular polygon, square, and/or rectangle shape. The size of the cross-sectional profile of the tubular member 760 can be at least approximately equal to a cross-sectional profile of the thread 80 and/or the needle 758 positioned therein. The lumen can permit axial and rotational movement of the thread 80 and needle 758, relative to the longitudinal axis of the lumen. The shape or size can vary along the length or width of the tubular member 760.

The handle 752 can be positioned along the distal portion of the tubular member 760. The handle 752 can comprise a proximal portion, a distal portion, and a longitudinal axis between the proximal and distal portions. The handle 752 can also comprise a passage 766 that extends between the proximal and distal portions of the handle 752. The passage 766 can be aligned with respect to the longitudinal axis of the handle 752. In some embodiments, the tubular member 760 can extend at least partially through the passage 766 of the handle 752. The tubular member 760 can also extend only partially through the passage 766 of the handle 752. For example, a distal portion of the tubular member 760 can be coupled with the proximal portion of the handle 752 so that the lumen of the tubular member 760 extends continuously with the passage 766. However, in some embodiments, the tubular member 760 can extend through an entirety of the passage 766 of the handle 752.

In accordance with some embodiments, the handle 752 can comprise first and second gripping mechanisms 762, 764. The first gripping mechanism 762 can extend from the first arm 754 toward the longitudinal axis 768 of the passage 766. The second gripping mechanism 764 can extend from the second arm 756 toward the longitudinal axis 768 of the passage 766.

The first and second gripping mechanisms 762, 764 can be movable to engage the tubular member 760, the needle 758, and/or the thread 80 extending through a passage 766 of the handle 752. Similar to the insertion devices 600, 700 discussed above, the passage 766 of the handle 752 can extend between the proximal and distal portions of the handle 752. In some embodiments, the tubular member 760 can extend at least partially through the passage 766 of the handle 752. The tubular member 760 can also extend only partially through the passage 766 of the handle 752. For example, a distal portion of the tubular member 760 can be coupled with the proximal portion of the handle 752 so that the lumen of the tubular member 760 extends continuously with the passage 766. However, in some embodiments, the tubular member 760 can extend through an entirety of the passage 766 of the handle 752.

Further, in some embodiments, a pass-through clearance for the needle can be changed in order to selectively engage or release the tubular member, the needle, and/or the thread extending through the passage to permit or restrict movement of the needle and/or the thread through the passage, relative to the insertion device. For example, in some embodiments, the size of the lumen of the tubular member 760 can be changed, e.g., increased or reduced, to selectively engage or release the tubular member 760, the needle 758, and/or the thread 80 extending through the passage to permit or restrict movement of the needle 758 and/or the thread 80 through the passage 766, relative to the insertion device 750. The change of the size of the lumen of the tubular member 760 can pinch down onto the needle 758, as shown in FIG. 4, and allow the physician to advance the needle 758 into the patient and thereafter release the needle 758 and/or the thread 80 by releasing compression on the tubular member 760 to permit the needle 758 and/or the thread 80 to move relative to the handle 752.

In the present embodiment illustrated in FIGS. 2-5, the passage 766 extends through and is formed at least partially by the first and second gripping mechanisms 762, 764, as explained below. Further, a longitudinal axis 768 of the passage 766 can extend through the passage 766 in a body component 769 of the handle 752 and through the first and second gripping mechanisms 762, 764.

The insertion device 750 can comprise a cap 706 that can be coupled to the handle 752 and enclose a portion of the thread 80 or the needle 758. The cap 706 can comprise a cavity that extends from a proximal portion toward a distal portion. The outer surface of the cap 706 can taper from the proximal portion toward the distal portion. The cap 706 is coupled to the handle 752 by inserting the distal portion of the handle 752 into the cavity of the cap 706. The cross-sectional profile of the outer surface of the handle 752 and the inner surface of the cap 706 can be configured to provide a friction fit between the handle 752 and the cap 706.

The cap 706 can be coupled to the insertion device 750 in the disengaged or engaged configuration, and with or without the thread 80 and needle 758 positioned therein. The insertion device 750 can comprise the cap 706 coupled to the handle 752 with the thread 80 and needle 758 positioned therein, such that a physician removes the cap 706 prior to operation if the insertion device 750. The cap 706 can comprise any of the features of a support member or cover member described in the present application.

Figure 3:
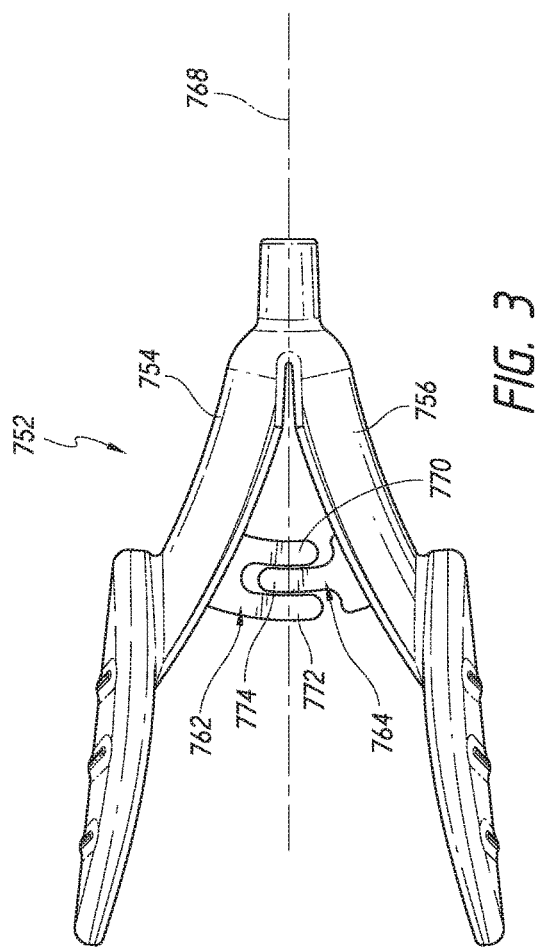
FIG. 3 is a side view of an insertion device, according to some embodiments.

Referring to FIG. 3, the first gripping mechanism 762 can comprise first and second portions 770, 772. Further, the second gripping mechanism 764 can comprise an interstitial portion 774 that can be positioned between the first and second portions 770, 772 when the device 750 is in a compressed, actuated state (shown in FIG. 3). Each of the first and second portions 770, 772 and the interstitial portion 774 can comprise apertures that extend therethrough to form the passage 766 and facilitate engagement with the tubular member 760, the needle 758, and/or the thread 80 extending through the passage 766.

For example, the first and second portions 770, 772 can comprise or form an aperture or slot 780, and the interstitial portion 774 can comprise or form an aperture or slot 782. The longitudinal axes 790, 792 of the apertures or slots 780, 782 can be aligned or misaligned with respect to each other in order to compress or release the tubular member 760 (and the needle 758 extending through the tubular member 760). Further, in some embodiments, the longitudinal axis 768 of the passage 766 can be aligned with respect to the longitudinal axes 790, 792 of the apertures 780, 782 when the device 750 is in the disengaged, actuated state, as shown in FIG. 5. However, when the device 750 is in a default, unactuated, engaged state, as shown in FIG. 4, the size of the lumen of the tubular member 760 is reduced because the apertures 780, 782 are offset. Thus, when the longitudinal axes 790, 792 of the apertures 780, 782 become offset relative to the longitudinal axis 768 of the passage 766, the pass-through clearance for the needle 758 and/or the thread 80 is reduced, thus restricting movement of the needle 758 and/or the thread 80 relative to the handle 752. Accordingly, in some embodiments, the size of the lumen of the tubular member 760 can be changed based on the positioning of the first and second gripping mechanisms 762, 764 and the apertures 780, 782 relative to each other.

Further, in some embodiments, each of the first and second gripping mechanisms 762, 764 can comprise a protrusion having a contact surface along an interior portion thereof that can contact or squeeze the outer surface of the tubular member 760 therebetween. In some embodiments, for one or both of the first or second gripping mechanisms 762, 764, the protrusions can form an enclosed aperture or slot (e.g., apertures 780, 782). However, in one or both of the first or second gripping mechanisms 762, 764, the protrusion extending therefrom can, with a corresponding protrusion from another of one or both of the first or second gripping mechanisms 762, 764, collectively form an enclosure that can at least partially surround a tubular member (e.g., the tubular member 760, as shown in FIGS. 4 and 5). These structures can be selectively manipulated, as discussed above, in order to permit the physician to engage the needle 758 and/or the thread 80 during the procedure. Although the embodiment illustrated in FIGS. 2-5 illustrates that the first and second portions 770, 772 and the interstitial portion 774 are positioned outside of the passage 766, other embodiments can be provided in which the first and second portions 770, 772 and the interstitial portion 774 are positioned inside of the passage 766.

In accordance with some embodiments, the first and second gripping mechanisms 762, 764 can extend along an arcuate path between their respective proximal and distal portions. Thus, the first and second gripping mechanisms 762, 764 can have complementary shapes or opposing facing surfaces that can slide along each other as the first and second arms 754, 756 pivot during compression of the first and second arms 754, 756 toward each other.

For example, FIG. 3 illustrates a default state in which the insertion device 750 is in an unactuated, engaged, biased position. In this default state, the first and second arms 754, 756 are positioned so that the longitudinal axes 790, 792 of at least one of the apertures 780, 782 is misaligned with respect to each other (and in some embodiments, with respect to the longitudinal axis 768 the passage 766 of the tubular member 760) to decrease a cross-sectional profile of the passage 766. In the default state, the first or second gripping mechanisms 762, 764 can overlap, such that the longitudinal axes 790, 792 of the apertures 780, 782 are partially aligned. Thus, the handle 752 can be formed in the default state and be deflectable away from the default state to disengage with or permit relative movement of the needle 758 and/or the thread 80 relative to the handle 752.

When the insertion device 750 is in the default state, the tubular member 760 can extend through the apertures 780, 782. However, because the longitudinal axes 790, 792 of the apertures 780, 782 are misaligned, opposing inner surfaces of the apertures 780, 782 will contact the outer surface of the tubular member 760 (or needle 758), thereby reducing the inner surface cross-sectional profile of the lumen of the tubular member 760 and partially engaging the needle 758 or thread 80 disposed therewithin. Thus, the default state of the insertion device 750 can provide secure engagement of the needle 758 to restrict movement of the needle 758 along the longitudinal axis 768.

In an actuated state, shown in FIG. 4, the first and second arms 754, 756 are compressed by the physician and urged toward the passage 766 such that the first or second gripping mechanisms 762, 764 converge towards each other to align the longitudinal axes 790, 792 of the apertures 780, 782 with the longitudinal axis 768 of the passage 766, thereby increasing a cross-sectional profile of the passage 766.

In operation, the needle 758 (coupled at its proximal end to the thread 80) are positioned in the lumen of the tubular member 760 of the insertion device 750. The first and second arms 754, 756 can be actuated or compressed towards each other in order to provide sufficient pass-through clearance to position a portion of the needle 758 between the first and second arms 754, 756 of the handle 752, within the engagement area of the first and second gripping mechanisms 762, 764. The distal portion of the needle 758 can extend from the distal portion of the handle 752.

To insert the needle 758 and thread 80 into the patient, the insertion device 750 can be directed toward a patient's skin with the device in the default state. As noted above, at least one of the first and second arms 754, 756 can be biased, in the default state, such that a portion at least one of the first and second arms 754, 756 engages the needle 758 to restrict movement of the needle 758 relative to the handle 752. In the default state, with the longitudinal axes 790, 792 of the apertures 780, 782 being misaligned relative to the longitudinal axis 768 of the passage 766, opposing contact surfaces of the apertures 780, 782 can contact the tubular member 760 (or the needle 758 if no tubular member 760 is used). Thus, the first or second gripping mechanisms 762, 764 can extend into the passage 766 of the tubular member 760 to decrease a cross-sectional profile of the passage 766 and prevent axial movement of the needle 758 when the distal portion of the needle 758 is inserted into the patient.

After the needle 758 has been initially inserted into the patient, further insertion of the needle 758 and thread 80 into the patient can be achieved by actuating the first and second arms 754, 756 insertion device 750 and carefully proximally retracting the device 750 relative to the needle 758. As discussed above, the insertion device 750 can be moved to the actuated state by pinching or compressing the first and second arms 754, 756 toward each other, such that the longitudinal axes 790, 792 of the apertures 780, 782 become aligned with respect to each other. As the apertures 780, 782 align, the inner cross-sectional profile of the lumen of the tubular member 760 is increased, thereby releasing engagement with the needle 758 (changing from engagement in FIG. 4 to the disengagement FIG. 5). The insertion device 750 can then be moved or slide backwards toward the proximal portion of the needle 758. Once in position, the arms 754, 756 can be released to permit the insertion device 750 to return to the default state, such that first or second gripping mechanisms 762, 764 pinch the lumen of the tubular member 760 to decrease a cross-sectional profile of the lumen, thereby engaging and preventing axial movement of the needle 758 relative to the device 750. The needle 758 can then be further inserted into the patient or out of the patient through a second portion of the patient's skin. The needle 758 can then be withdrawn from the patient and the handle 752 can be retracted relative to the patient.

Figure 8:
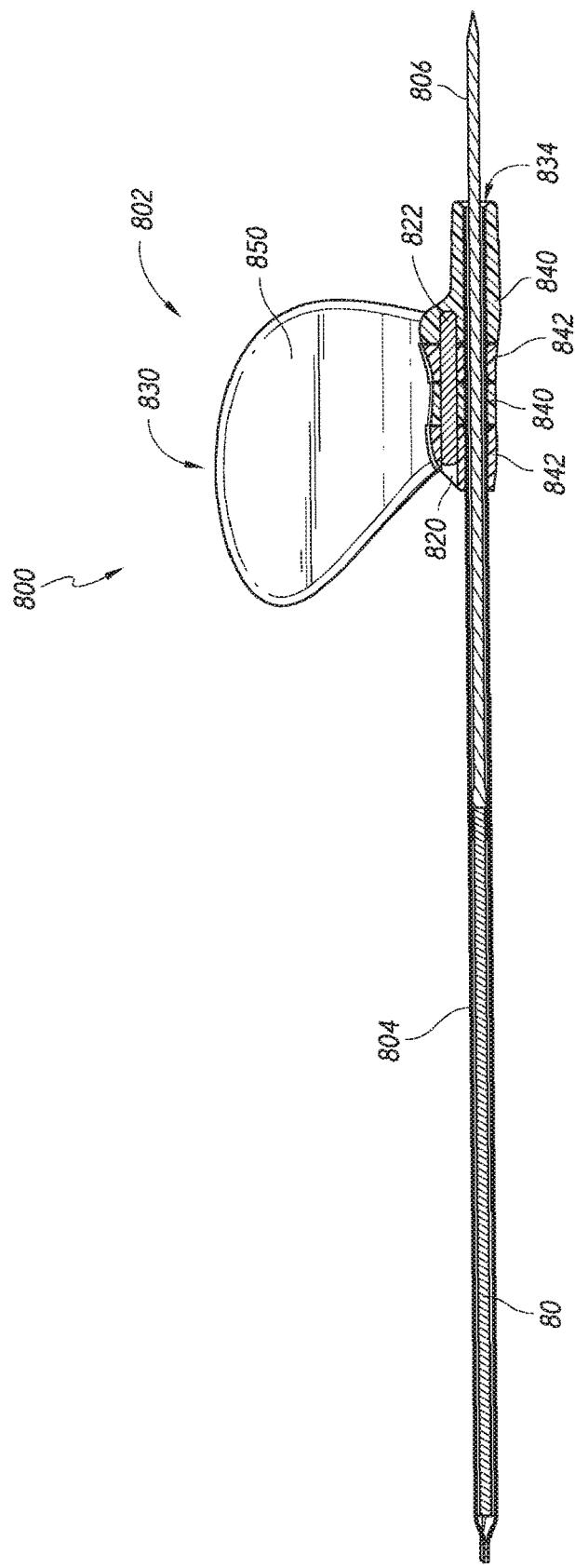
FIG. 8 is a cross-sectional side view of an insertion device, according to some embodiments.

Referring now to FIGS. 6-8, an embodiment of a needle insertion device is illustrated that can engage with a needle by compressing opposing wings toward each other, thereby allowing a physician to advance the needle and the thread to a desired position in situ. The wings can thereafter be released to disengage with the needle. FIG. 6-8 illustrate an insertion device 800 that can comprise a handle 802 that can be coupled to a tubular member 804. As similarly discussed above with respect to the embodiments shown in FIGS. 2-5, the insertion device 800 can be configured to engage or release a needle 806 positioned within a passage of the device 800 as the device is actuated by the physician.

In some embodiments, the device can comprise first and second butterfly mechanisms, each comprising a wing, a pivot component, and a knuckle portion. The knuckle portions can each comprise an aperture extending therethrough. The pivot components of the first and second butterfly mechanisms can be aligned along a pivot axis to permit the first butterfly mechanism to pivot relative to the second butterfly mechanism. The first and second butterfly mechanisms can pivot between first and second positions. In the first position, central axes the apertures can be coaxially aligned with respect to each other to permit a needle or trocar to move through the apertures relative to the assembly. In the second position, the central axes of the first and second apertures can be misaligned with respect to each other to engage a trocar positioned through the first and second apertures to restrict movement of the trocar relative to the assembly.

The handle 802 can comprise a proximal portion, a distal portion opposite the proximal portion, and a pivot cavity 820 that can extend between and/or connect the proximal and distal portions of the handle 802, as illustrated in FIGS. 7 and 8. The pivot cavity 820 can comprise a cavity that extends along a longitudinal axis from the proximal portion toward the distal portion of the handle 802. The pivot cavity 820 can comprise a passage that extends through the proximal and distal portions of the handle 802. The pivot cavity 820 can be configured to receive a pivot pin 822. A cross-sectional profile of the pivot cavity 820 and the pivot pin 822 can permit portions of the handle 802 to pivot about the longitudinal axis of the pivot cavity 820.

The handle 802 can comprise a first handle portion 830 and second handle portion 832. The first and second handle portions 830, 832 can each comprise a pivot coupling, actuation components on a first side of the pivot coupling, and engagement components coupled to the actuation components and disposed on a second side of the pivot coupling. The physician can actuate first and second handle portions 830, 832 by pinching or separating the actuation components, thereby causing the actuation components and the engagement components to pivot about the pivot coupling. In some embodiments, the engagement components can collectively form a passage or aperture 834 whose size can change based on the relative positioning of the engagement components.

Thus, as discussed above with respect to other embodiments, the passage 834 of the handle 802 can be configured to permit the tubular member 804, the needle 806, and/or a HA thread 80 to extend through the passage 834. The passage 834 can extend along a longitudinal axis between the proximal and distal portions of the handle 802. In some embodiments, the longitudinal axis of the passage 834 can extend parallel to the longitudinal axis of the pivot cavity 820. In some embodiments, the pivot cavity 820 and the passage 834 can extend parallel to each other through the knuckle portions 840, 842.

In accordance with some embodiments, the first and second handle portions 830, 832 can be coupled about the pivot pin 822, such that first and second handle portions 830, 832 can move or pivot about the longitudinal axis of the pivot pin, relative to each other and the passage 834. The first and second handle portions 830, 832 can each comprise a knuckle portion 840, 842. The first handle portion 830 can comprise a first knuckle portion 840, and the second handle portion 832 can comprise a second knuckle portion 842. Each knuckle portion 840, 842 can comprise a portion of the pivot cavity 820 and the passage 834. The first and second knuckle portions 840, 842 can be coupled together with the pivot pin 822 such that the first and second handle portions 830, 832 can move or pivot around the longitudinal axis of the pivot cavity 820, relative to each other and the passage 834. Further, the knuckle portions 840, 842 can each comprise an aperture or section of the passage. For example, the first and second knuckle portions 840, 842 can each comprise apertures whose longitudinal axes can be aligned to be coaxial in order to provide a maximum pass-through clearance and maximum lumen cross-section of the passage 834, or misaligned along the longitudinal axis of the passage 834 in order to reduce the pass-through clearance or reduce the lumen cross-section of the passage 834.

The tubular member 804 can be coupled with the handle 802. Similar to the insertion devices 600, 750 discussed above, the tubular member 804 can extend at least partially through the passage 834 of the handle 802. The tubular member 804 can also extend only partially through the passage 834 of the handle 802. For example, a distal portion of the tubular member 804 can be coupled with the proximal portion of the handle 802 so that the lumen of the tubular member 804 extends continuously with the passage 834. However, in some embodiments, the tubular member 804 can extend through an entirety of the passage 834 of the handle 802.

In some embodiments, each of the first and second handle portions 830, 832 can comprise an arm. The first handle portion 830 can comprise a first arm 850, and the second handle portion 832 can comprise a second arm 852. The first and second arms 850, 852 can each comprise a proximal portion and a distal portion. The proximal portions of the first and second arms 850, 852 can be coupled to a respective knuckle portion 840, 842, such that the distal portions of the first and second arms 850, 852 extends outwardly from the knuckle portions 840, 842. The first and second arms 850, 852 can extend outwardly from the knuckle portions 840, 842 relative to the longitudinal axis of the pivot cavity 820. The proximal portions of the first and second arms 850, 852 can comprise a longitudinal axis that extends transverse relative to the longitudinal axis of the pivot cavity 820. The distal portions of the first and second arms 850, 852 can comprise longitudinal axes that extend transverse relative to longitudinal axes of the knuckle portion 840, 842.

The insertion device 800 can comprise a disengaged and engaged configuration. In the disengaged configuration, the first and second arms 850, 852 are pivoted around the longitudinal axis of the pivot cavity 820 to align passages through the first and second knuckle portions 840, 842. The knuckle portions 840, 842 can extend along a surface of the lumen with the passages of the first and second knuckle portions 840, 842 aligned. In the disengaged configuration, the needle 806 is not prevented or restricted from movement through the passage 834 relative to handle 802.

In the engaged configuration, the first and second arms 850, 852 can be compressed toward each other around the longitudinal axis of the pivot cavity 820, such that the first and/or second knuckle portions 840, 842 pivot and the apertures of the first and second knuckle portions 840, 842 move apart from each other, thus reducing the pass-through clearance cross-sectional profile the lumen of the passage 834. In the engaged configuration, movement of the needle 806 positioned in the passage 834 is restricted along the longitudinal axis of the passage 834. As with the other embodiments disclosed herein, the physician can advance or retract the needle 806 by squeezing or actuating the device 800 to the engaged configuration.

Referring now to FIGS. 9-12, additional embodiments of insertion devices employing engagement mechanisms similar to those discussed above with regard to the embodiment shown in FIGS. 1-8 are shown.

FIGS. 9 and 10 illustrate another embodiment of an insertion device that can comprise an engagement mechanism that can be actuated to engage or disengage with a needle. FIGS. 9 and 10 illustrate an insertion device 900 can comprise a tubular member 902, a handle 904, and a needle 906 coupled to a HA thread 80. Similar to the embodiments illustrated above with respect to FIGS. 2-8, the handle 904 can comprise a moveable portion that can be actuated to shift an aperture through which the needle 906 passes, in order to engage and/or release the needle 906.

The handle 904 comprises a proximal portion, a distal portion, and a longitudinal axis between the proximal and distal portions. A passage or lumen 908 having a longitudinal axis 909 that extends through the handle 904, between the proximal and distal portions. The lumen 908 can be aligned with respect to the longitudinal axis of the handle 904.

The handle 904 can be coupled with the tubular member 902, in any of the manners discussed above, such as that disclosed above with respect to FIGS. 2-8, which will not be repeated here for brevity. The handle 904 can comprise a cavity 910 that extends from the outer surface of the handle toward the lumen 908. The cavity can extend across or intersect a longitudinal axis of the lumen 908. The cavity can intersect the longitudinal axis of the lumen 908 at the distal portion of the handle 904. The cavity can comprise a channel, a notch, and/or an open space that intersects the lumen.

The handle 904 can comprise a moveable engagement member 920 that can be positioned within the cavity 910. The engagement member 920 can be formed separately from the handle 904. However, in some embodiments, the moveable engagement member 920 can alternatively be formed unitarily with the handle 904. The moveable engagement member 920 can be coupled to the handle 904 by a hinge, a biasing member (e.g., a spring), and/or a sliding coupling. When the moveable engagement member 920 is positioned in the cavity 910, an outer or proximal portion of the moveable engagement member 920 can be positioned adjacent to an outer surface of the handle 904. The inner or distal portion of the moveable engagement member 920 can extend into the cavity 910 and be positionable across the lumen 908 to selectively engage or disengage the needle 906 and/or the thread 80. The engagement can be by an interference or friction engagement. For example, some embodiments can incorporate the engagement mechanism disclosed in FIGS. 4-6 of U.S. patent application Ser. No. 15/414,219, filed on the same day as the present Application, the entirety of which is incorporated herein by reference.

For example, the distal portion of the engagement member 920 can comprise an engagement member passage 922 that can extend through a portion of the moveable engagement member 920. The passage 922 of the moveable engagement member 920 can form a portion of the lumen 908 that extends through the cavity 910. The moveable engagement member passage 922 can comprise a groove or aperture that extends along an outer surface or through the moveable engagement member 920. The passage 922 can extend through a cross-section of the moveable engagement member 920. When the moveable engagement member 920 is positioned in the cavity 910, the moveable engagement member passage 922 extends along the moveable engagement member 920 parallel to the longitudinal axis of the lumen 908.

Further, the engagement member 920 can be moved between an engaged configuration and a disengaged configuration in order to selectively engage the needle 906 and/or the thread 80 positioned within the lumen 908. For example, a longitudinal axis 924 of the passage 922 can be displaced relative to the longitudinal axis 909 of the lumen 908 in order to engage with the needle 906 and/or the thread 80 extending through the passage 922 (FIG. 10 illustrates the longitudinal axis 924 being parallel to and aligned with or coincident with the longitudinal axis 909 of the lumen 908). In order to release or permit movement of the needle 906 and/or thread 80 extending through the passage 922, the longitudinal axis 924 of the passage 922 can be aligned with the longitudinal axis 909 of the lumen 908.

In some embodiments, an extension 930 can extend from a portion of the moveable engagement member 920 toward the handle 904. The extension 930 can protrude from the proximal portion of the moveable engagement member 920. The extension can protrude toward the proximal and/or distal portions of the handle 904. The extension 930 can extend along and/or be coupled to an outer surface of the handle 904. A portion of the extension 930 can engage the handle 904 in order to bias the engagement member 920 to the disengaged configuration and/or to restrict movement of the moveable engagement member 920 into the cavity 910.

In accordance with some embodiments, the engagement member 920 can be biased to an engaged or disengaged configuration. In order to urge the moveable engagement member 920 relative to the longitudinal axis of the lumen 908, a biasing member can be positioned between the moveable engagement member 920 and the tubular member 902. The biasing member can be positioned between the moveable engagement member 920 and the handle 904 to urge the moveable engagement member 920 toward or away from the longitudinal axis of the lumen 908. In some embodiments, the biasing member can comprise a spring that couples the engagement member 920 to a bottom portion of the cavity 910. The biasing member can both couple the engagement member 920 to the handle 904 and urge the engagement member 920 to either the engaged or disengaged configuration in a default state. When the physician actuates the engagement member 920, the passage 922 can release or engage with the needle 906 and/or thread 80.

As illustrated FIG. 10, the needle 906 can be positioned within the handle 904, such that the proximal portion of the needle 906 can extend within the lumen 908 of the handle and the moveable engagement member passage 922. The proximal portion of the needle 906 can be positioned within the moveable engagement member passage 922, and the distal portion of the needle 906 can extend out of distal portion of the handle 904.

In the engaged configuration, the moveable engagement member 920 can restrict movement of the needle 906 relative to the longitudinal axis of the lumen 908. As noted above, in the engaged configuration, the longitudinal axis 924 of the moveable engagement member passage 922 can be offset from the longitudinal axis 909 of the lumen 908. Movement of the needle 906 can be restricted by engagement of the distal portion of the moveable engagement member 920 against the needle 906. The moveable engagement member 920 can be in the engaged configuration when the moveable engagement member 920 is moved to urge the extension 930 or biasing member.

In the disengaged configuration, the moveable engagement member 920 can permit movement of the needle 906 relative to the longitudinal axis of the lumen 908. In the disengaged configuration, the longitudinal axis 909 of the lumen 908 can be aligned with or made coincident with respect to the longitudinal axis 924 of the moveable engagement member passage 922. The moveable engagement member 920 can be in the disengaged configuration when the moveable engagement member 920 is moved to urge the extension 930 or biasing member.

To insert the needle 906 and thread 80 into the patient, the insertion device 900 can be configured in the engaged configuration to engage and prevent axial movement of the needle 906. The insertion device 900 can be directed toward a patient's skin so that the distal portion of the needle 906 pierces the skin and permits movement of the needle 906 into the patient. Further advancement of the needle 906 and thread 80 into the patient can be performed by disengaging the insertion device 900 from the needle 906 and carefully sliding the insertion device 900 proximally over the needle 906. The physician can then actuate the compression on the engagement member 920 in order to cause the insertion device 900 to move to the engaged configuration and continue advancing the needle 906 and thread 80 into the patient.

FIGS. 11 and 12 illustrates an insertion device 950 that can operate to engage a needle and/or thread, as discussed above with respect to any of the embodiments illustrated in FIGS. 2-10. However, FIGS. 11 and 12 illustrate an optional thread-protection feature that can be incorporated into any of the embodiments disclosed herein. As illustrated, the insertion device 950 can comprise a handle or body 952, an engagement mechanism 954, and a tubular member 956. The engagement mechanism 954 can comprise a portion of the insertion device 950 (e.g., a handle thereof) and any of the features or functions discussed above with respect FIGS. 2-10, which will not be repeated here for brevity. Further, any of the engagement mechanisms of the embodiments discussed above with respect to FIGS. 2-10, as well as the engagement mechanism 954, can be configured to rebound (via a spring or biasing mechanism, for example) to a first position after moving from the first position to a second position (whether the first position is one in which the needle is engaged or disengaged).

The tubular member 956 can advantageously protect and maintain a HA thread 80 and/or a needle 958 coupled to the thread 80. The tubular member 956 can comprise a proximal portion, a distal portion, and a longitudinal axis between the proximal and distal portions. The proximal portion of the tubular member 956 can comprise a cavity 960. The cavity 960 can comprise an enclosure extending proximally from the engagement member that can house at least a portion of the thread 80 and the needle 958 therewithin. The cavity 960 can have a cross-section profile size that is greater than a diameter or cross-sectional profile of the thread 80, to permit a portion of the thread to gather within the cavity 960.

In practice, the needle 958 can extend from a lumen 970 of the device 950, with a proximal portion of the needle 958 being engaged by the engagement mechanism 954. The physician can operate the device 950 similar to that already discussed above, which will not be repeated here for brevity. However, as shown in FIG. 12, the entirety of the thread 80 and a portion of the needle 958 can remain unexposed during handling of the device 950 prior to and/or during the procedure. This can enable the physician to ensure that the thread 80 and needle 958 remain clean and intact prior to use.

In some embodiments, the tubular member 956 can be formed from a single, continuous piece of material with the handle 952. However, in some embodiments, the tubular member 956 can also be removably coupled to the handle 952. For example, the tubular member 956 can be detached from the handle 952 in order to load a needle 958 and thread 80 into the device 950. The tubular member 956 can then be coupled to the handle 952 with the thread 80 enclosed therein.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A thread insertion assembly comprising: a tubular member comprising a proximal portion, a distal portion, and a lumen extending between the proximal and distal portions; and a handle comprising a body component coupled to the tubular member, the body component comprising a passage that extends in communication with the lumen, the handle further comprising first and second arms coupled to the body component and extending outwardly from the distal portion of the tubular member, wherein the first arm comprises a first gripping mechanism extending from the first arm toward the second arm, and the second arm comprises a second gripping mechanism extending from the second arm toward the first arm, and wherein the first gripping mechanism comprises a first protrusion, the second gripping mechanism comprises a second protrusion, and the tubular member extends through an enclosure formed by the first and second protrusions; wherein in a first configuration, a portion of at least one of the first or second gripping mechanisms is positioned along the passage to define a first cross-sectional clearance, and in a second configuration, the portion of at least one of the first or second gripping mechanisms is extends along the passage to define a second cross-sectional clearance, different from the first cross-sectional clearance, to change a cross-sectional profile of the passage.

Clause 2. The thread insertion assembly of Clause 1, wherein the tubular member is compressed by the portion of at least one of the first or second gripping mechanisms in the first configuration.

Clause 3. The thread insertion assembly of any one of the preceding Clauses, comprising a trocar positioned within the passage, wherein in the second configuration, the trocar is engaged by the tubular member.

Clause 4. The thread insertion assembly of Clause 3, comprising a thread coupled to the trocar, wherein the thread extends along the proximal portion of the tubular member.

Clause 5. The thread insertion assembly of any one of the preceding Clauses, wherein the first or second gripping mechanism is biased toward the first configuration.

Clause 6. The thread insertion assembly of any one of the preceding Clauses, wherein the first cross-sectional clearance is less than the second cross-sectional clearance.

Clause 7. The thread insertion assembly of any one of the preceding Clauses, wherein the tubular member extends through the passage and in the first configuration, the portion of at least one of the first or second gripping mechanisms compresses the lumen to decrease a cross-sectional profile of the lumen.

Clause 8. The thread insertion assembly of any one of the preceding Clauses, comprising a cap comprising a proximal portion a closed distal portion, and a cavity extending from the proximal portion toward the distal portion, wherein the proximal portion is configured to couple to a distal portion of the tubular member to enclose the lumen.

Clause 9. The thread insertion assembly of any one of the preceding Clauses, wherein the first and second protrusions comprise respective first and second passages.

Clause 10. The thread insertion assembly of Clause 9, wherein the first and second passages are offset from each other in the first configuration.

Clause 11. The thread insertion assembly of any one of the Clauses 9 to 10, wherein the first and second passages are aligned in the second configuration.

Clause 12. The thread insertion assembly of any one of the Clauses 9 to 11, wherein the first and second passages comprise tubular lumens having respective longitudinal axes that can be coaxially aligned in the second configuration.

Clause 13. The thread insertion assembly of any one of the preceding Clauses, wherein the each of the first and second protrusions comprises a grasping surface, wherein the grasping surface extends transverse to the respective first or second arm.

Clause 14. The thread insertion assembly of Clause 13, wherein each grasping surface comprises a ridge on a surface facing away from the passage.

Clause 15. The thread insertion assembly of any one of the preceding Clauses, wherein passage comprises a tubular lumen.

Clause 16. A method of inserting a thread comprising: biasing first and second arms of a handle to align a portion of first and second passages of the handle; positioning a portion of a trocar between the first and second passages of the handle; releasing the first and second arms such that a portion of the first and second arms engages a proximal portion of the trocar, wherein movement of the trocar, relative to the handle, is restricted; inserting a distal portion of a trocar into a patient; biasing the first and second arms of the handle to release the proximal portion of the trocar such that movement of the trocar, relative to the handle, is permitted; and retracting the handle relative to the patient.

Clause 17. The method of Clause 16, comprising positioning the trocar between the first and second passages of the handle such that the distal portion of the trocar extends from the handle.

Clause 18. The method of any one of the Clauses 16 to 17, wherein inserting a portion of the trocar into a patient comprises moving the handle toward the patient.

Clause 19. A thread insertion assembly comprising: a tubular member comprising a proximal portion, a distal portion, and a lumen extending between the proximal and distal portions; a handle coupled to the tubular member distal portion, the handle comprising a passage that extends in communication with the lumen and a cavity intersecting a portion of the passage, the handle comprising a moveable engagement member positioned within the cavity and having an inner surface forming a portion of the passage, the moveable engagement member having (i) a first position in which an inner surface of the engagement member is positioned along the passage to define a first cross-sectional clearance and (ii) a second position in which a portion of the engagement member extends along the passage to define a second cross-sectional clearance, different from the first cross-sectional clearance, to change a cross-sectional profile of the passage; and a trocar positioned within the distal portion of the passage; wherein in an obstructing configuration, the engagement member restricts axial movement of the trocar relative to the passage, and in an open configuration, the engagement member permits axial movement of the trocar relative to the passage.

Clause 20. The thread insertion assembly of Clause 19, wherein the engagement member is biased toward the obstructing configuration.

Clause 21. The thread insertion assembly of any one of the Clauses 19 to 20, wherein the engagement member is biased toward the open configuration.

Clause 22. The thread insertion assembly of any one of the Clauses 19 to 21, comprising a spring positioned between the engagement member and the tubular member to provide a biasing force to bias the engagement member toward the obstructing configuration or the open configuration.

Clause 23. The thread insertion assembly of any one of the Clauses 19 to 22, wherein the engagement member comprises a proximal portion and a distal portion, and wherein the proximal portion comprises an extension configured to engage a portion of the tubular member and restrict movement of the distal portion into the cavity.

Clause 24. The thread insertion assembly of any one of the Clauses 19 to 23, wherein the trocar is engaged by the movable member in an interference fit in the first position to restrict axial movement of the trocar relative to the passage.

Clause 25. The thread insertion assembly of any one of the Clauses 19 to 24, wherein the engagement member comprises a passage having a cross-sectional profile that is greater than a cross-sectional profile of an outer surface of the trocar.

Clause 26. The thread insertion assembly of any one of the Clauses 19 to 25, wherein the engagement member comprises an outer surface having a groove configured to permit movement of the trocar relative to the tubular member.

Clause 27. The thread insertion assembly of any one of the Clauses 19 to 26, comprising a thread coupled to the trocar, wherein the thread extends along the proximal portion of the tubular member.

Clause 28. A method of inserting a thread comprising: positioning a moveable engagement member within a cavity of a handle such that the engagement member is accessible by a user; positioning a trocar within a passage of the handle such that a proximal portion of the trocar extends through a lumen of a tubular member and the passage of the handle, the trocar being engageable by the engagement member when disposed within the passage; inserting a distal portion of the trocar into a patient; moving the engagement member to release the trocar; and retracting the tubular member relative to the patient.

Clause 29. The method of Clause 28, wherein the trocar extends through an aperture of the engagement member and the engagement member is biased to cause the aperture to be misaligned with respect to the passage to engage the engagement member with the trocar, and wherein the moving the engagement member comprises axially aligning the aperture with the passage to disengage the engagement member from the trocar to permit axial movement of the trocar relative to the aperture and the passage.

Clause 30. The method of Clause 29, wherein the moving the engagement member to release the trocar comprises moving the engagement member relative to the cavity to permit axial movement of the trocar relative to the aperture and the passage.

Clause 31. The method of any one of the Clauses 28 to 30, wherein the trocar extends through an aperture of the engagement member and the engagement member is biased to cause the aperture to be aligned with respect to the passage to disengage the engagement member from the trocar, and wherein the positioning the trocar comprises moving the engagement member to axially misalign the aperture with the passage to engage the engagement member against the trocar to restrict axial movement of the trocar relative to the aperture and the passage.

Clause 32. The method of Clause 31, wherein the moving the engagement member comprises releasing the engagement member to align the aperture and the passage to permit axial movement of the trocar relative to the aperture and the passage.

Clause 33. A thread insertion assembly comprising: a first butterfly mechanism comprising a first wing, a first pivot component, and a first knuckle portion, the first knuckle portion comprising a first aperture extending therethrough; a second butterfly mechanism comprising a second wing, a second pivot component, and a second knuckle portion, the second knuckle portion comprising a second aperture extending therethrough, the first and second pivot components being aligned along a pivot axis to permit the first butterfly mechanism to pivot relative to the second butterfly mechanism, the first and second butterfly mechanisms being pivotable between (i) a first position in which central axes the first and second apertures are coaxially aligned with respect to each other to permit a trocar to move through the first and second apertures relative to the assembly and (ii) a second position in which the central axes of the first and second apertures are misaligned with respect to each other to engage a trocar positioned through the first and second apertures to restrict movement of the trocar relative to the assembly.

Clause 34. The thread insertion assembly of Clause 33, further comprising a tubular member coupled to the first knuckle portion of the first butterfly mechanism, the tubular member comprising a lumen having a central axis that is aligned with the central axis of the first aperture.

Clause 35. The thread insertion assembly of Clause 34, wherein the tubular member extends through the first aperture.

Clause 36. The thread insertion assembly of any one of the Clauses 34 to 35, wherein the tubular member extends through the first and second apertures.

Clause 37. The thread insertion assembly of Clause 36, wherein the tubular member is compressed by first and second knuckle portions when the first and second butterfly mechanisms are in the second position such that the trocar is engaged with the assembly to restrict movement of the trocar relative to the assembly.

Clause 38. The thread insertion assembly of any one of the Clauses 33 to 37, further comprising a trocar positioned within the first and second apertures.

Clause 39. The thread insertion assembly of Clause 38, further comprising a thread coupled to the trocar, wherein the thread extends within a tubular member coupled to the first butterfly mechanism.

Clause 40. The thread insertion assembly of any one of the Clauses 33 to 39, wherein the first pivot component is positioned between the first wing and the first knuckle portion.

Clause 41. The thread insertion assembly of any one of the Clauses 33 to 40, wherein the second pivot component is positioned between the second wing and the second knuckle portion.

Clause 42. The thread insertion assembly of any one of the Clauses 33 to 41, wherein a compressive force to urge the first wing toward the second wing causes the first and second butterfly mechanisms to move to the second position.

Clause 43. The thread insertion assembly of any one of the Clauses 33 to 42, wherein the first knuckle portion comprises a pair of first knuckles that are longitudinally spaced apart from each other along the central axis of the first aperture, each of the pair first knuckles comprising first apertures.

Clause 44. The thread insertion assembly of Clause 43, wherein the second knuckle portion comprises a pair of second knuckles that are longitudinally spaced apart from each other along the central axis of the second aperture, each of the pair second knuckles comprising second apertures, at least one of the second knuckles being positionable within a longitudinal gap between the pair of first knuckles to align the first apertures with the second apertures.

Clause 45. The thread insertion assembly of any one of the Clauses 33 to 44, further comprising a pivot pin that extends through the first and second pivot components to interconnect the first and second butterfly mechanisms.

Clause 46. A method of inserting a thread comprising: positioning a portion of a trocar into a first passage of a first arm and into a second passage of a second arm, the first and second arms being rotatable about a longitudinal axis; biasing the first and second arms to rotate the first and second arms about the longitudinal axis to engage the trocar positioned within the first and second passages; inserting a distal portion of a trocar into a patient; releasing the proximal portion of the trocar to permit movement of the trocar relative to the first and second arms is permitted; and retracting the handle relative to the patient.

Clause 47. The method of Clause 46, comprising positioning the trocar into the first and second passages of the handle such that the distal portion of the trocar extends from the first and second arms.

Clause 48. The method of any one of the Clauses 46 to 47, wherein inserting a portion of the trocar into a patient comprises moving the first and second arms toward the patient.

Clause 49. The method of any one of the Clauses 46 to 48, wherein the handle comprises a rotational axis offset from longitudinal axes of the first and second passages, and wherein the biasing the first and second arms comprises rotating the first and second passages about the rotational axis.

Clause 50. The method of Clause 49, wherein the first arm comprises a first butterfly mechanism having a first wing, and the second arm comprises a second butterfly mechanism having a second wing, wherein the first and second wings are rotated toward each other as the first and second butterfly mechanisms are rotated about the longitudinal axis.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A thread insertion assembly comprising:
   a tubular member comprising a proximal portion, a distal portion, and a lumen extending between the proximal and distal portions; and
   a handle comprising a body component coupled to the tubular member, the body component comprising a passage that extends in communication with the lumen, the handle further comprising first and second arms coupled to the body component and extending outwardly from the distal portion of the tubular member, wherein the first arm comprises a first gripping mechanism extending from the first arm toward the second arm, and the second arm comprises a second gripping mechanism extending from the second arm toward the first arm, and wherein the first gripping mechanism comprises a first protrusion, the second gripping mechanism comprises a second protrusion, and the tubular member extends through an enclosure formed by the first and second protrusions;
   wherein in a first configuration, a portion of at least one of the first or second gripping mechanisms is positioned along the passage to define a first cross-sectional clearance, and in a second configuration, the portion of at least one of the first or second gripping mechanisms extends along the passage to define a second cross-sectional clearance, greater than the first cross-sectional clearance, to change a cross-sectional profile of the passage.

2. The thread insertion assembly of claim 1, wherein the tubular member is compressed by at least one of the first or second gripping mechanisms in the first configuration.

3. The thread insertion assembly of claim 1, comprising a trocar positioned within the passage, wherein in the second configuration, the trocar is engaged by the tubular member.

4. The thread insertion assembly of claim 3, comprising a thread coupled to the trocar, wherein the thread extends along the proximal portion of the tubular member.

5. The thread insertion assembly of claim 1, wherein the first or second gripping mechanism is biased toward the first configuration.

6. The thread insertion assembly of claim 1, wherein the tubular member extends through the passage and in the first configuration, the portion of at least one of the first or second gripping mechanisms compresses the lumen to decrease a cross-sectional profile of the lumen.

7. The thread insertion assembly of claim 1, wherein the first and second protrusions comprise respective first and second passages.

8. The thread insertion assembly of claim 7, wherein the first and second passages are offset from each other in the first configuration.

9. The thread insertion assembly of claim 7, wherein the first and second passages are aligned in the second configuration.

10. The thread insertion assembly of claim 1, wherein the first or second gripping mechanism is biased toward the second configuration.

11. The thread insertion assembly of claim 1, wherein the first protrusion extends to a first distal end portion and the second protrusion extends to a second distal end portion, and wherein the first distal end portion is interposed between the second distal end portion and the second arm, and the second distal end portion is interposed between the first distal end portion and the first arm.

12. The thread insertion assembly of claim 1, wherein the first protrusion is interposed between the second protrusion and the second arm, the second protrusion is interposed between the first protrusion and the first arm.

13. A thread insertion assembly comprising:
a body component having a passage that extends through the body component, the passage defining an axis; and
first and second arms coupled to the body component and extending outwardly from the axis, wherein the first arm comprises a first gripping mechanism extending from the first arm toward the second arm, and the second arm comprises a second gripping mechanism extending from the second arm toward the first arm, and wherein the first gripping mechanism comprises a first protrusion, the second gripping mechanism comprises a second protrusion, and an enclosure is formed by the first and second protrusions;
a tubular member extending through the enclosure;
wherein in a first configuration, a portion of at least one of the first or second gripping mechanisms is positioned along the passage to define a first cross-sectional clearance, and in a second configuration, the portion of at least one of the first or second gripping mechanisms extends along the passage to define a second cross-sectional clearance, greater than the first cross-sectional clearance, to change a cross-sectional profile of the passage.

14. The thread insertion assembly of claim 13, further comprising a trocar extending through the enclosure, wherein in the first configuration, a portion of at least one of the first or second gripping mechanisms is engaged against the trocar, and in the second configuration, the portion of at least one of the first or second gripping mechanisms is spaced apart from the trocar.

15. The thread insertion assembly of claim 14, comprising a thread coupled to the trocar, wherein the thread extends along a proximal portion of the tubular member.

16. The thread insertion assembly of claim 14, wherein the tubular member extends through the passage and in the first configuration, the portion of at least one of the first or second gripping mechanisms compresses a lumen of the tubular member to decrease a cross-sectional profile of the lumen.

17. The thread insertion assembly of claim 13, wherein, in the first configuration, a portion of at least one of the first or second gripping mechanism resists movement of a trocar relative to the body component, and the second configuration, the portion of at least one of the first or second gripping mechanism permits movement of the trocar relative to the body component.

18. The thread insertion assembly of claim 13, wherein the first or second gripping mechanism is biased toward the first configuration.

19. The thread insertion assembly of claim 13, wherein the first or second gripping mechanism is biased toward the second configuration.

20. The thread insertion assembly of claim 13, wherein the first and second protrusions comprise respective first and second passages, and the enclosure extends through the first and second passages in the first and second configuration.

21. The thread insertion assembly of claim 13, wherein the first protrusion is interposed between the second protrusion and the second arm, the second protrusion is interposed between the first protrusion and the first arm, and the axis is interposed between the first and second protrusions.

22. A method of operating a thread insertion assembly, the method comprising:
providing a thread insertion assembly comprising a tubular member and a handle, the handle comprising a body component coupled to the tubular member, the body component comprising a passage that extends in communication with a lumen of the tubular member, the handle further comprising first and second arms coupled to the body component and extending outwardly from a distal portion of the tubular member, wherein the first arm comprises a first gripping mechanism extending from the first arm toward the second arm, and the second arm comprises a second gripping mechanism extending from the second arm toward the first arm, and wherein the first gripping mechanism comprises a first protrusion, the second gripping mechanism comprises a second protrusion, and the tubular member extends through an enclosure formed by the first and second protrusions, wherein in a first configuration, a portion of at least one of the first or second gripping mechanisms is positioned along the passage to define a first cross-sectional clearance, and in a second configuration, the portion of at least one of the first or second gripping mechanisms is positioned along the passage to define a second cross-sectional clearance, less than the first cross-sectional clearance, to change a cross-sectional profile of the passage;

positioning the assembly in the first configuration;

while maintaining the assembly in the first configuration, positioning a portion of a trocar through the passage; and positioning the assembly in the second configuration to engage the trocar within the passage.

23. The method of claim 22, further comprising, when engaged in the second configuration, inserting a distal portion of the trocar into a patient.

24. The method of claim 22, wherein the positioning the assembly in the first configuration comprises biasing the first and second arms toward the first configuration.

25. The method of claim 22, wherein the positioning the assembly in the second configuration comprises biasing the first and second arms toward the second configuration.

26. The method of claim 22, further comprising moving the first and second arms of the handle toward the first configuration permit the passage to open towards the first cross-sectional clearance for permitting disengagement and removal of the trocar from the assembly.

27. The method of claim 22, wherein the first protrusion is interposed between the second protrusion and the second arm, and the second protrusion is interposed between the first protrusion and the first arm.

* * * * *